US00PP26681P2

(12) United States Plant Patent
Zaiger et al.

(10) Patent No.: US PP26,681 P2
(45) Date of Patent: May 3, 2016

(54) NECTARINE TREE NAMED 'SWEET FIREGEM'

(50) Latin Name: ***Prunus persica* var. *nucipersica***
Varietal Denomination: Sweet Firegem

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 2 days.

(21) Appl. No.: 14/544,119

(22) Filed: Nov. 26, 2014

(51) Int. Cl.
*A01H 5/08* (2006.01)

(52) U.S. Cl.
USPC ..... Plt./190

(58) Field of Classification Search
USPC ..... Plt./190
CPC ..... A01H 5/0856
See application file for complete search history.

*Primary Examiner* — Kent L Bell

(57) ABSTRACT

A new and distinct variety of nectarine tree (*Prunus persica* var. *nucipersica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with a vigorous, upright growth habit.
2. Tree being a regular and productive bearer of large size fruit.
3. Fruit with firm, yellow flesh with good handling and shipping qualities.
4. Fruit with very good flavor and eating quality.
5. Fruit with an attractive red skin color.

1 Drawing Sheet

Botanical designation: *Prunus persica* var. *nucipersica*.
Variety denomination: 'Sweet Firegem'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of nectarine tree was originated and asexually reproduced by us in our experimental orchard located near Modesto, Stanilaus County, Calif.

PRIOR VARIETIES

Among the existing varieties of nectarine trees, which are known to us, and mentioned herein, 'Honey Lite' Nectarine (U.S. Plant Pat. No. 18,400) and 'Honey Haven' Nectarine (U.S. Plant Pat. No. 12,393).

STATEMENT REGARDING FEDERALLY SPONSORED RESEARCH AND DEVELOPMENT

Not applicable.

ORIGIN OF THE VARIETY

The new and distinct variety of nectarine tree *Prunus persica* var. *nucipersica* was developed by us in our experimental orchard located near Modesto, Calif. from open pollinated seed collected from the commercial variety 'Honey Lite' Nectarine (U.S. Plant. Pat. No. 18,400). A large number of these open pollinated seedlings were budded on established trees of 'Nemaguard' Rootstock (non-patented) to enhance earlier fruit production. Under close and careful observation the present seedling exhibited desirable fruit and tree characteristics and was selected in 2005 for additional asexual propagation and commercialization.

ASEXUAL REPRODUCTION OF THE VARIETY

In 2005 asexual reproduction of the new and distinct variety of nectarine tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new and distinct variety of nectarine tree is of large size, vigorous, upright growth and a regular and productive bearer of large size, yellow flesh, clingstone fruit. The fruit is further characterized by having attractive red skin color with very good flavor and eating quality. In comparison to its seed parent 'Honey Lite' Nectarine (U.S. Plant Pat. No. 18,400) the fruit of the new variety has an higher average Brix of 16.0° compared to 11.7° and is slightly larger in size. In comparison to the commercial variety 'Honey Haven' Nectarine (U.S. Plant Pat. No. 12,393) the fruit of the new variety is approximately 16 days earlier in maturity.

DESCRIPTION OF THE PHOTOGRAPH

The accompanying color photographic illustration shows typical specimens of the foliage and fruit of the present new nectarine variety.

The illustration shows the upper and lower surface of the leaves, an exterior and sectional view of a single fruit divided in its suture plane to show flesh color, pit cavity and the stone remaining in place.

The photographic illustration was taken shortly after being picked (shipping ripe) from a 9 year old tree and the colors are as nearly true as is reasonably possible in a color representation of this type.

DESCRIPTION OF THE VARIETY

The following is a detailed botanical description of the new variety of nectarine tree, its flowers, foliage and fruit, as based on observations of 9 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters the first growing season. Varies slightly with soil type, fertility of soil and climatic conditions.

*Form*.—Upright, usually pruned to vase shape.

*Branching habit*.—Upright, crotch angle approximately 35°, increases with heavy crop load.

*Productivity*.—Productive, thinning and spacing of fruit necessary for desired marketable size. Fruit set varies with climatic conditions during bloom time.

*Bearer*.—Regular, has had adequate fruit set 7 consecutive years. No alternate bearing observed.

*Fertility*.—Self-fertile.

*Density*.—Medium dense, pruning to vase shape desirable for sunlight penetration to center of tree to enhance fruit color and health of fruit wood.

*Hardiness*.—Hardy in all stone fruit growing areas of California. Tree grown in USDA Hardiness Zone 9. Winter chilling requirement approximately 400 hours at or below 45° F.

Trunk:

*Size*.—Medium to large. Average circumference 54.6 cm at 22.9 cm above ground on a 9 year old tree.

*Stocky*.—Medium stocky.

*Texture*.—Medium shaggy, roughness increases with age.

*Color*.—Varies from 5GY 3/4 to 7.5Y 3/4.

Branches:

*Size*.—Medium. Average circumference 17.5 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 20 in a 25.8 square cm area. Average length 4.6 mm. Average width 2.3 mm. Color varies from 10YR 6/8 to 10YR 5/10.

*Color*.—New growth varies from 5GY 5/8 to 5GY 6/6. Mature growth varies from 10YR 4/4 to 10YR 3/4, varies with age of growth.

Leaves:

*Size*.—Large. Average length 137.6 mm. Average width 36.5 mm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Small to medium. Average length 11.5 mm. Average width 1.7 mm. Color varies from 5GY 6/8 to 5GY 5/8. Longitudinally grooved. Surface — glabrous.

*Glands*.—Type — reniform. Number varies from 3 to 5, average number 4. Size — large. Average length 1.3 mm. Average diameter 1.1 mm. Located primarily on base of leaf blade and upper portion of petiole. Color varies from 5GY 7/8 to 2.5GY 7/10.

*Stipules*.—Average number 2. Average length 7.0 mm. Margin — pectinate. Color varies from 5GY 6/6 to 5GY 5/8.

*Color*.—Upper surface varies from 5GY 3/6 to 5GY 4/6. Lower surface varies from 5GY 5/4 to 5GY 6/4. Midvein color varies from 2.5GY 6/6 to 5GY 6/6.

Flower buds:

*Size*.—Medium to large. Average length 17.5 mm. Average diameter 11.6 mm.

*Hardiness*.—Hardy with respect to California winters.

*Density*.—Medium dense.

*Form*.—Conical, becoming elongated just before opening.

*Pedicel*.—Average length 4.7 mm. Average width 1.5 mm. Color varies from 5GY 7/6 to 5GY 6/6. Surface — glabrous.

*Color*.—Varies from 7.5RP 6/10 to 7.5RP 8/4.

Flowers:

*Blooming period*.—Date of First Bloom Feb. 1, 2014. Date of Petal Fall Feb. 11, 2014, varies slightly with climatic conditions.

*Size*.—Medium to large, showy. Average height 19.5 mm. Average diameter 38.9 mm.

*Petals*.—Normally 5, alternately arranged to sepals. Petal apex — rounded. Petal base — rounded to somewhat truncated. Size — large. Average length 20.0 mm. Average width 16.8 mm. Form — obovate. Margin — sinuate. Arrangement — overlapping. Color varies from 7.5RP 8/4 to 5RP 9/2, fades with age of growth. Both upper and lower surfaces glabrous.

*Sepals*.—Normally 5, alternately arranged to petals. Size — large. Average length 6.7 mm. Average width 5.5 mm. Shape — ovate, apex rounded to triangular. Margin — entire. Color — upper surface varies from 2.5GY 4/4 to 5GY 5/6. Lower surface varies from 2.5R 3/4 to 5R 3/6. Upper surface glabrous, lower surface pubescent.

*Stamens*.—Average number per flower 42. Average filament length 15.6 mm. On average, the stamens are slightly above the height of the petals. Filament color varies from N 9.5/(white) to 5RP 5/10 depending on age of flower. Anther color varies from 7.5R 4/12 to 2.5Y 8/10.

*Pollen*.—Self fertile. Color varies from 2.5Y 8/10 to 2.5Y 7/12.

*Pistil*.—Normally one. Surface — glabrous. Average length 18.2 mm. Position of stigma even with anthers. Color varies from 2.5GY 8/6 to 2.5GY 8/8.

*Fragrance*.—Heavy.

*Color*.—Varies from 7.5RP 8/4 to 5RP 9/2.

*Pedicel*.—Average length 4.3 mm. Average width 1.3 mm. Color varies from 5GY 7/6 to 5GY 6/6. Surface — glabrous.

*Number flowers per flower bud*.—Normally 1.

Fruit:

*Maturity when described*.—Firm ripe and ready for consumption.

*Date of first picking*.—May 31, 2014.

*Date of last picking*.—Jun. 9, 2014, varies slightly with climatic conditions.

*Size*.—Large. Average diameter axially 63.3 mm. Average transversely in suture plane 69.0 mm. Average weight 193.1 grams, varies slightly with fertility of the soil, amount of thinning and climatic conditions.

*Form*.—Globose.

*Suture*.—Nearly smooth, extends from base to apex.

*Ventral surface*.—Smooth.

*Apex*.—Retuse.

*Base*.—Retuse.

*Stem cavity*.—Rounded to slightly elongated in suture plane. Average depth 8.2 mm. Average diameter 7.2 mm.

Stem:

*Size*.—Small. Average length 8.9 mm. Average diameter 3.3 mm.

*Color*.—Varies from 10Y 6/8 to 2.5GY 5/8.

Flesh:

*Ripens*.—Evenly.

*Texture*.—Firm, meaty.

*Fibers*.—Few, small, tender.

*Firmness*.—Firm, comparable to other commercial varieties.

*Aroma*.—Slight.

*Amydgalin*.—Undetected.

*Eating quality*.—Very good.

*Flavor*.—Very good, good balance between acid and sugar.

*Juice*.—Moderate amount, enhances flavor.

*Acidity*.—Not available.

*Brix*.—Average Brix 16.0°, varies slightly with amount of fruit per tree and climatic conditions.

*Color*.—Varies from 2.5Y 8.5/12 to 5Y 8/10.

*Pit cavity*.—Average length 39.2 mm. Average width 28.9 mm. Average depth 11.9 mm. Color 5Y 8/10.

Skin:

*Thickness*.—Medium.

*Surface*.—Smooth.

*Pubescence*.—Wanting.

*Tendency to crack*.—None.

*Color*.—Ground color varies from 2.5Y 8.5/12 to 2.5Y 8/10. Overspread with 7.5R 2/6 to 7.5R 3/12.

*Tenacity*.—Tenacious to flesh.

*Astringency*.—Undetected.

Stone:

*Type*.—Clingstone, strong adherence to flesh.

*Size*.—Large. Average length 38.2 mm. Average width 27.9 mm. Average thickness 21.8 mm.

*Form*.—Obovoid.

*Base*.—Flat.

*Apex*.—Pointed. Average length 1.7 mm.

*Surface*.—Pitted throughout, pits vary from round to elongated. One shallow groove on each side of suture extending from base to apex.

*Sides*.—Unequal, one side extending further outward from suture plane.

*Ridges*.—Very small and short, extending from base towards apex.

*Tendency to split*.—None.

*Color*.—Varies from 7.5YR 6/6 to 10YR 6/6 when dry.

Kernel:

*Size*.—Large. Average length 18.5 mm. Average width 12.2 mm. Average depth 6.4 mm.

*Form*.—Ovoid.

*Viability*.—Partially viable, some embryos have incomplete development.

*Skin color*.—Varies from 5Y 9/4 to 7.5Y 9/4.

Use:

*Dessert*.—Market — local and long distance.

Keeping quality: Good, held firm in cold storage for 3 weeks at 38° to 42° F. without internal breakdown or appreciable loss of flavor.

Shipping quality: Good, showed minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of nectarine tree, (*Prunus persica* var. *nucipersica*) substantially as illustrated and described.

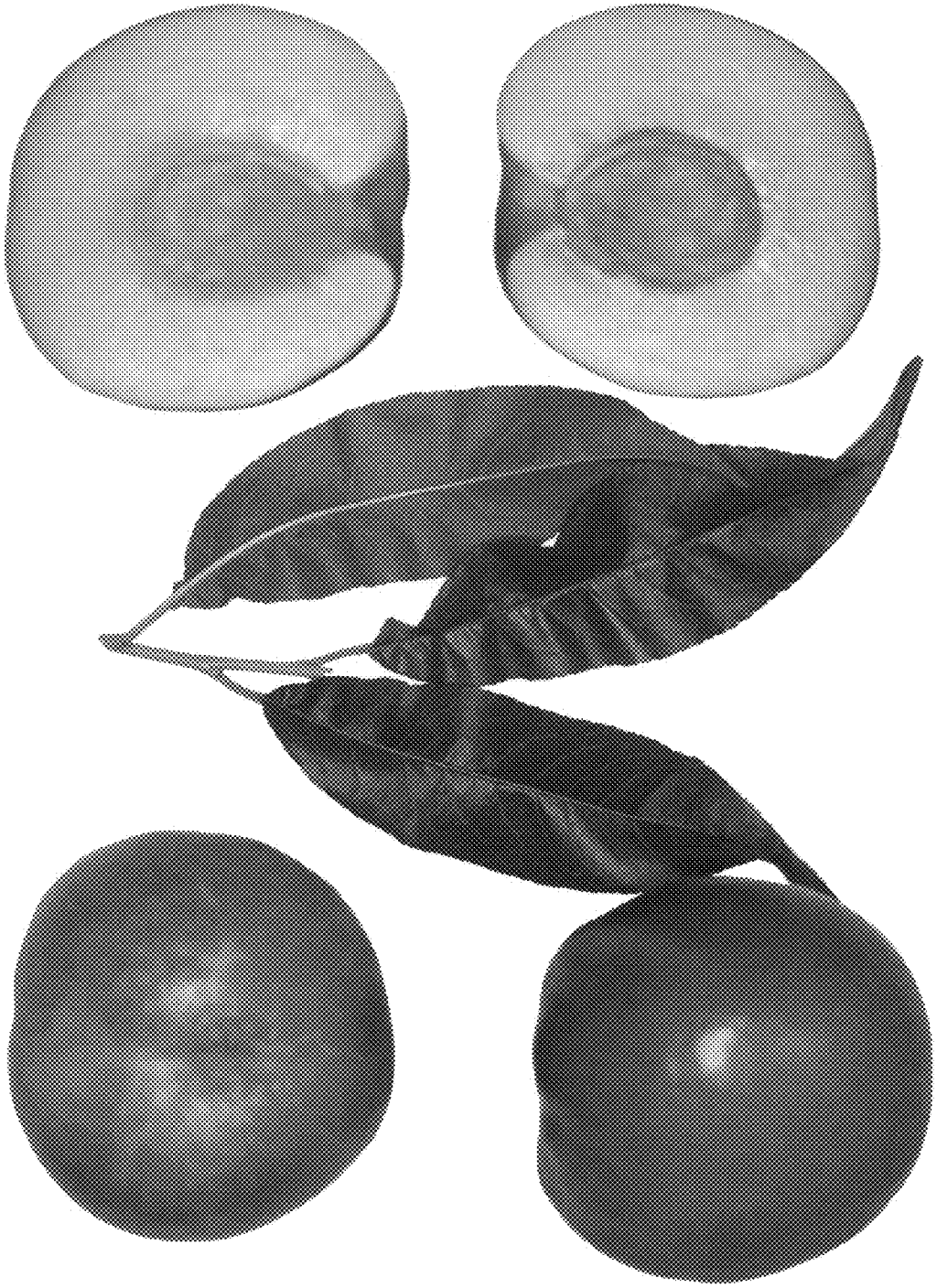

* * * * *